US006432108B1

(12) United States Patent
Burgess et al.

(10) Patent No.: US 6,432,108 B1
(45) Date of Patent: Aug. 13, 2002

(54) TRANSVERSE CONNECTOR

(75) Inventors: Ian C. Burgess, Barrington, RI (US); Hassan A. Serhan, Easton, MA (US); Michael S. Varieur, Portsmouth, RI (US); Felix G. Quevedo, Miami, FL (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/490,664

(22) Filed: Jan. 24, 2000

(51) Int. Cl.[7] .............................................. A61B 17/70
(52) U.S. Cl. .......................................... 606/61; 606/60
(58) Field of Search .............................. 606/60, 61, 57, 606/105

(56) References Cited

U.S. PATENT DOCUMENTS

| 483,342 A | 9/1892 | Bolte |
| 900,717 A | 10/1908 | Feaster |
| 3,019,504 A | 2/1962 | Castagliuolo |
| 3,752,203 A | 8/1973 | Hill, Jr. |
| 4,011,602 A | 3/1977 | Rybicki et al. |
| 4,085,744 A | * 4/1978 | Lewis et al. .................. 606/61 |
| 4,179,905 A | 12/1979 | Schultenkämper |
| 4,289,124 A | 9/1981 | Zickel |
| 4,411,259 A | 10/1983 | Drummond |
| 4,611,580 A | 9/1986 | Wu |
| 4,611,581 A | 9/1986 | Steffee |
| 4,648,388 A | 3/1987 | Steffee |
| 4,653,481 A | 3/1987 | Howland et al. |
| 4,655,199 A | 4/1987 | Steffee |
| 4,658,809 A | 4/1987 | Ulrich et al. |
| 4,696,290 A | 9/1987 | Steffee |
| 4,719,905 A | 1/1988 | Steffee |
| 4,763,644 A | 8/1988 | Webb |
| 4,771,767 A | 9/1988 | Steffee |

(List continued on next page.)

FOREIGN PATENT DOCUMENTS

| DE | 867 422 | 2/1953 |
| DE | 3639810 A1 | 5/1988 |
| EP | 0 128 058 A1 | 12/1984 |
| EP | 0 242 708 A2 | 10/1987 |
| FR | 2 615 095 | 11/1988 |
| FR | 2 624 720 | 6/1989 |
| GB | 167228 | 7/1921 |
| GB | 2 173 104 A | 10/1986 |
| RU | 286136 | 11/1970 |
| RU | 1823791 A3 | 6/1993 |
| WO | WO 87/00160 | 1/1987 |
| WO | WO 91/16020 | 10/1991 |

*Primary Examiner*—Jeffrey A. Smith
*Assistant Examiner*—Michael B. Priddy
(74) *Attorney, Agent, or Firm*—Maginot, Moore & Bowman, LLP

(57) ABSTRACT

A transverse connector for a spinal column corrective device for interconnecting two components connectable with vertebrae of a spinal column includes a first member having a body portion and a connector portion extending from the body portion, the connector portion including an opening for receiving the first component, a second member having a body portion and a connector portion extending from the body portion, the connector portion including an opening for receiving the second component, and a clamp extending between the first and second member body portions, the clamp being movable into a tightened position to lock the first and second members into position relative to one another, and a loosened position to permit adjustment of the position of the first and second members relative to one another. The first and second member body portions having mating retaining surfaces to prevent relative movement between the first and second members when the clamp is in the tightened position.

18 Claims, 10 Drawing Sheets

U.S. PATENT DOCUMENTS

| | | | |
|---|---|---|---|
| 4,805,602 A | | 2/1989 | Puno et al. |
| 4,815,453 A | | 3/1989 | Cotrel |
| 4,887,595 A | | 12/1989 | Heinig et al. |
| 4,913,134 A | | 4/1990 | Luque |
| 4,950,269 A | | 8/1990 | Gaines, Jr. |
| 5,005,562 A | * | 4/1991 | Cotrel .................. 606/61 |
| 5,010,879 A | * | 4/1991 | Moriya et al. ............. 606/61 |
| 5,067,955 A | | 11/1991 | Cotrel |
| 5,113,685 A | | 5/1992 | Asher et al. |
| 5,116,334 A | | 5/1992 | Cozad et al. |
| 5,120,171 A | | 6/1992 | Lasner |
| 5,127,912 A | | 7/1992 | Ray et al. |
| 5,154,718 A | | 10/1992 | Cozad et al. |
| 5,176,680 A | | 1/1993 | Vignaud et al. |
| 5,190,543 A | | 3/1993 | Schläpfer |
| 5,207,678 A | | 5/1993 | Harms et al. |
| 5,261,907 A | | 11/1993 | Vignaud et al. |
| 5,261,913 A | | 11/1993 | Marnay |
| 5,282,801 A | | 2/1994 | Sherman |
| 5,360,431 A | | 11/1994 | Puno et al. |
| 5,395,370 A | * | 3/1995 | Muller et al. ............. 606/61 |
| 5,423,818 A | | 6/1995 | Van Hoeck et al. |
| 5,437,671 A | | 8/1995 | Lozier et al. |
| 5,454,812 A | | 10/1995 | Lin |
| 5,514,132 A | | 5/1996 | Csernátony et al. |
| 5,522,816 A | * | 6/1996 | Dinello et al. .......... 606/61 |
| 5,527,314 A | | 6/1996 | Brumfield et al. |
| 5,531,747 A | | 7/1996 | Ray |
| 5,562,662 A | | 10/1996 | Brumfield et al. |
| 5,562,663 A | | 10/1996 | Wisnewski et al. |
| 5,601,552 A | * | 2/1997 | Cotrel .................. 606/61 |
| 5,609,592 A | | 3/1997 | Bumfield et al. |
| 5,616,142 A | * | 4/1997 | Yuan et al. ............. 606/61 |
| 5,620,444 A | * | 4/1997 | Assaker ................ 606/61 |
| 5,624,442 A | | 4/1997 | Mellinger et al. |
| 5,667,507 A | | 9/1997 | Corin et al. |
| 5,688,272 A | | 11/1997 | Montague et al. |
| 5,707,372 A | | 1/1998 | Errico et al. |
| 5,709,684 A | | 1/1998 | Errico et al. |
| 5,716,355 A | | 2/1998 | Jackson et al. |
| 5,743,911 A | | 4/1998 | Cotrel |
| 5,752,955 A | | 5/1998 | Errico |
| 5,885,284 A | | 3/1999 | Errico et al. |
| 5,899,903 A | | 5/1999 | Cotrel |
| 5,980,521 A | | 11/1999 | Montague et al. |
| 5,980,523 A | * | 11/1999 | Montague et al. ....... 606/61 |
| 6,083,226 A | | 7/2000 | Fiz |
| 6,110,173 A | | 8/2000 | Thomas, Jr. |
| 6,113,600 A | | 9/2000 | Drummond et al. |
| 6,126,660 A | * | 10/2000 | Dietz .................. 606/61 |
| 6,136,003 A | | 10/2000 | Hoeck et al. |
| 6,139,548 A | * | 10/2000 | Errico .................. 606/61 |
| 6,217,578 B1 | * | 4/2001 | Crozet et al. ........... 606/61 |
| 6,234,705 B1 | * | 5/2001 | Troxell ................ 403/237 |
| 6,238,396 B1 | * | 5/2001 | Lombardo ............. 606/61 |

* cited by examiner

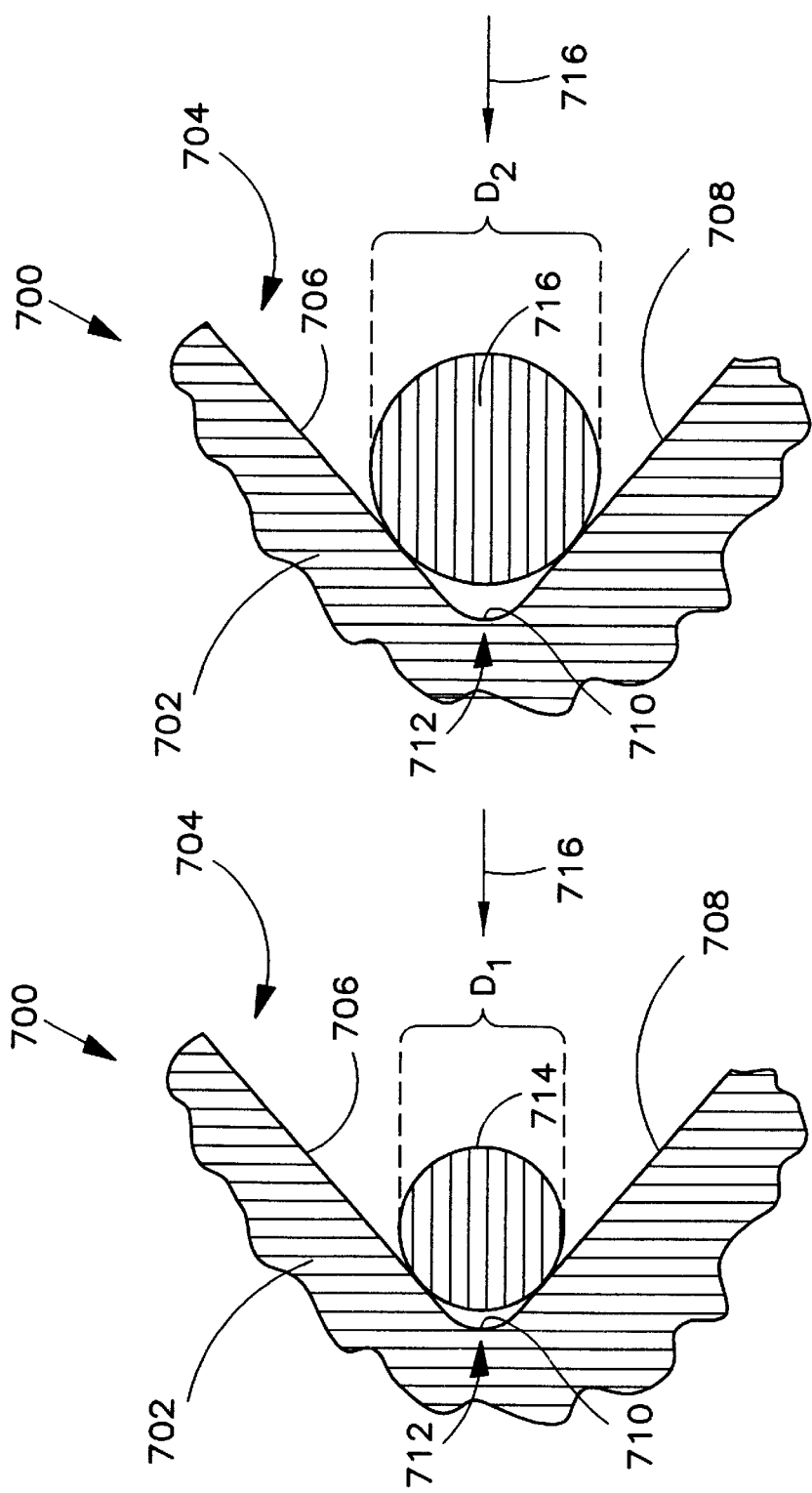

US 6,432,108 B1

TRANSVERSE CONNECTOR

BACKGROUND OF THE INVENTION

The present invention relates generally to connectors for interconnecting components of a spinal column corrective device such as longitudinal members, hooks, and/or pedicle screws, and more particularly to a cross-link or transverse connector which is adjustable longitudinally to accommodate a variety of spacings between such components.

Longitudinal members of spinal column corrective devices generally extend longitudinally along the spinal column. Each longitudinal member, which may consist of a rod or a plate, for example, is typically attached to the spinal column with hooks or pedicle screws which are connected to the longitudinal member. The longitudinal members may be connected together using transverse connectors. Each transverse connector forms a bridge between two longitudinal members to strengthen the overall structure of the spinal column corrective device and provide a desired spacing between longitudinal members.

SUMMARY OF THE INVENTION

The present invention is a transverse connector for interconnecting components of a spinal column corrective device, for example, a pair of longitudinal members which are connected to vertebrae of a spinal column. As is further explained below, the present invention might be readily adapted to interconnect a longitudinal member and a pedicle screw, a pair of screws, a longitudinal member and a hook, a pair of hooks, or a pedicle screw and a hook. One embodiment of the present transverse connector generally includes a first member which is adjustably connected to a second member to provide a plurality of selectable spacings between the longitudinal members. The first member includes a body portion having retaining surfaces for engaging similar retaining surfaces on the body portion of the second member, an intermediate portion extending from the body portion having an opening for receiving a clamp or set screw, and a connector portion extending from the intermediate portion for engaging the longitudinal member. When the set screw is turned into the intermediate portion opening, it clamps a first longitudinal member within the first member connector portion. The second member also includes an intermediate portion extending from the body portion having an opening for receiving a clamp or set screw, and a connector portion extending from the intermediate portion for engaging a second longitudinal member. When the set screw is turned into the intermediate portion opening, it clamps the second longitudinal member within the second member connector portion.

The first and second members are connected to one another by a clamp such that when the clamp is in a tightened position, the retaining surfaces of the first and second member engage one another to lock the members in position relative to one another, thereby fixing the distance between the longitudinal members. When the clamp is in a loosened position, the first and second members may remain connected to one another while the retaining surfaces are spaced apart from one another, and the members are adjusted longitudinally relative to one another to a different position. During adjustment, guides extending from the body portion of the second member maintain the first and second members in alignment.

The transverse connector of the present invention may be attached to the longitudinal members of a spinal column corrective device after the longitudinal members have been fastened to the vertebrae of the spinal column. The clamp of the present invention is loosened so that the first and second members may be adjusted relative to one another longitudinally. The members are adjusted until the distance between the two connector portions roughly corresponds to the distance between the longitudinal members. The set screws are backed out of their respective openings. The connector portions are then placed into engagement with the longitudinal members, and the set screws are turned into their respective openings to engage the longitudinal members and clamp the longitudinal members against the connector portions. The distance between the longitudinal members may be adjusted, if desired, as described above. Once a desired spacing is achieved, the clamp is tightened to lock the first and second members in position relative to one another.

BRIEF DESCRIPTION OF THE DRAWINGS

The foregoing and other features of the invention will become more apparent and the invention will be better understood upon consideration of the following description taken in conjunction with the accompanying drawings, wherein:

FIG. 11 is a cross-sectional view of the connector portion of still another embodiment of the transverse connector of the present invention with a first longitudinal member positioned within the connector portion.

FIG. 12 is a view similar to FIG. 11, but showing a second longitudinal member positioned within the connector portion of the transverse connector of FIG. 11.

DESCRIPTION OF EMBODIMENTS OF THE INVENTION

The embodiments described herein are not intended to be exhaustive or to limit the invention to the precise forms disclosed. Rather, the embodiments selected for description are described to permit those skilled in the art to utilize their teachings.

Figure 1:
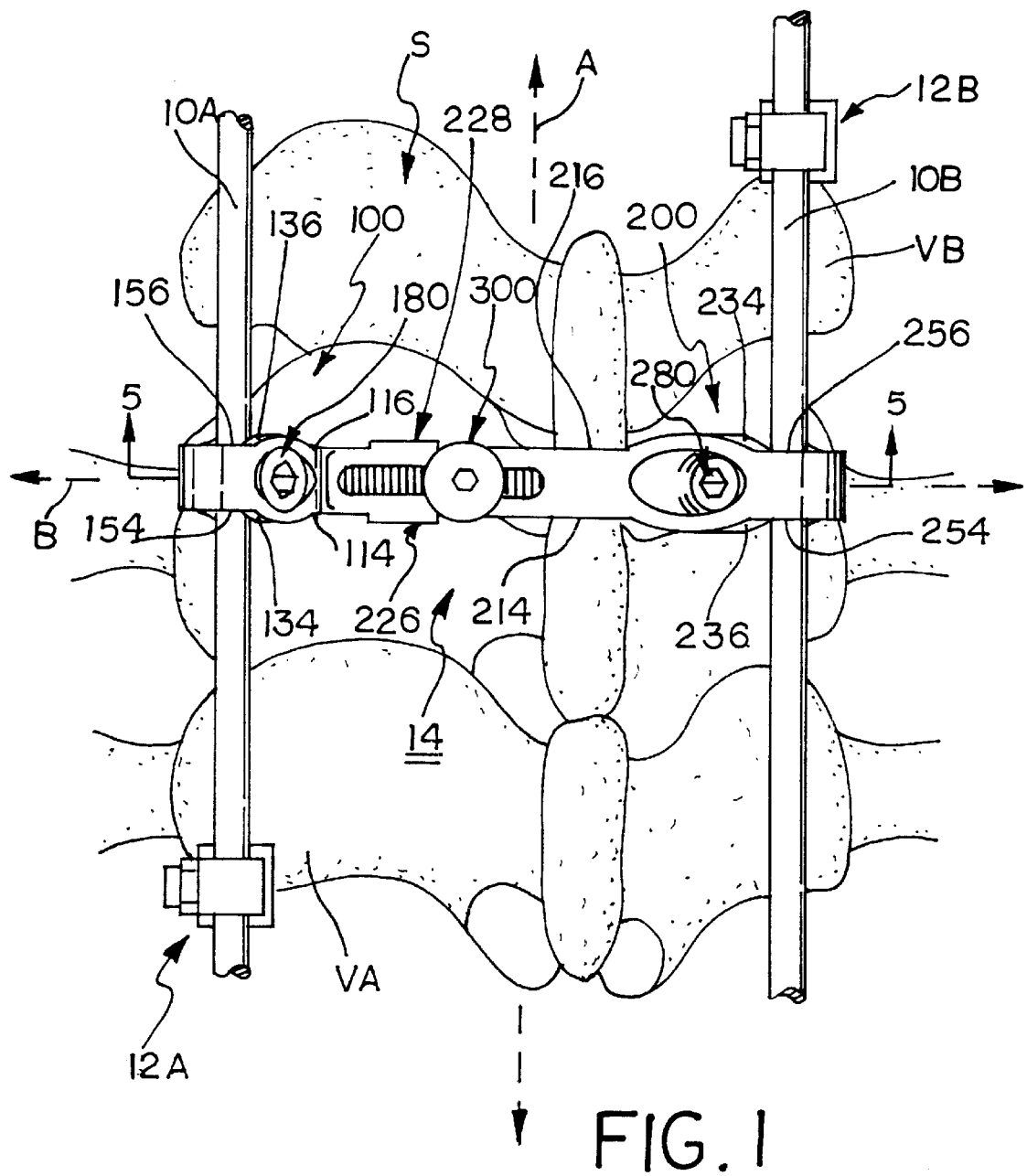
FIG. 1 is a partially fragmented, top plan view of one embodiment of the transverse connector of the present invention interconnecting a pair of longitudinal members which are connected to a spinal column.
Figure 2:
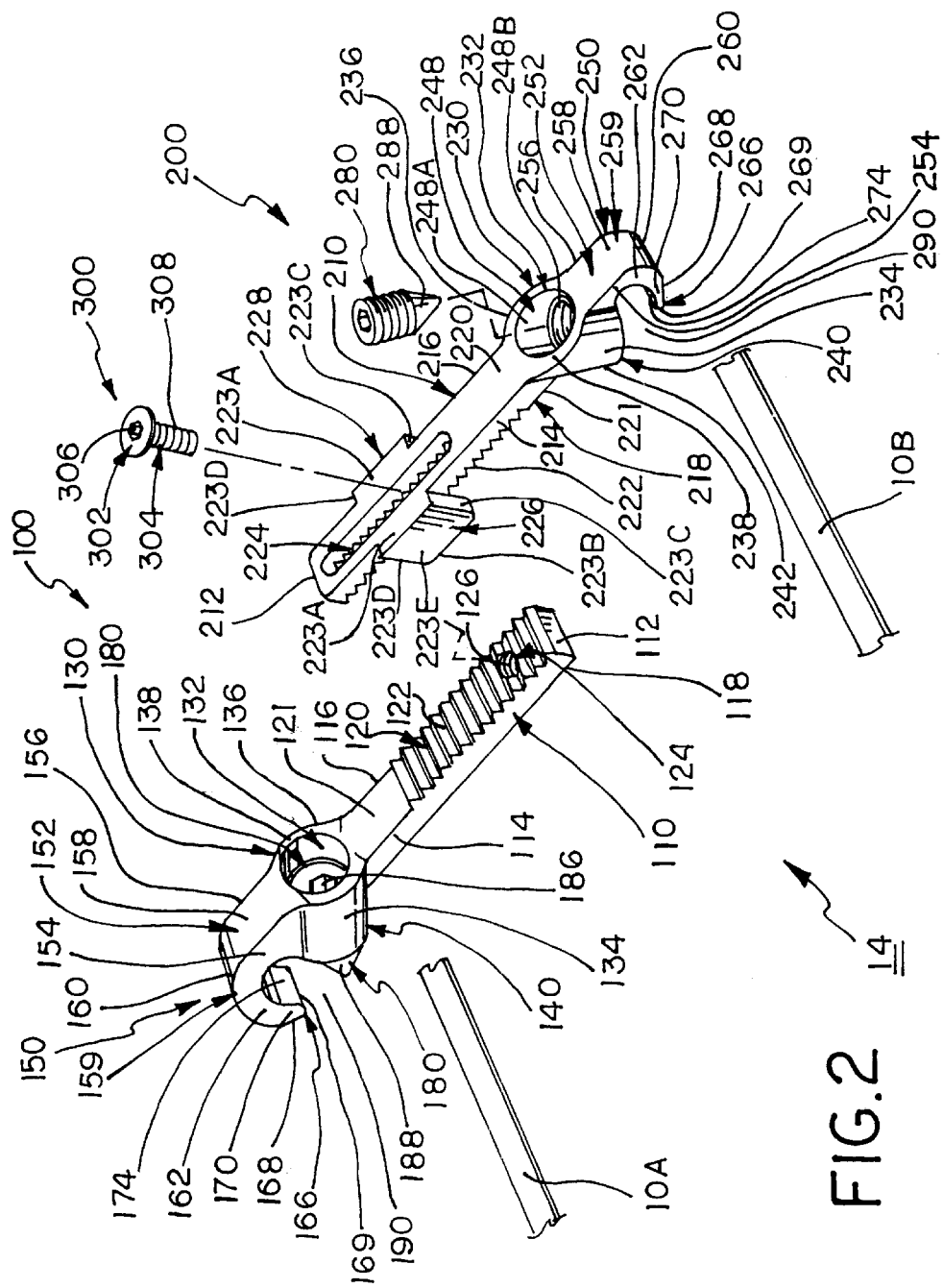
FIG. 2 is an exploded perspective view of the transverse connector of FIG. 1.

As shown in FIG. 1, a spinal column corrective device may include longitudinal members 10A and 10B (shown as rods which extend longitudinally, substantially parallel to a longitudinal axis A of the spinal column S. Longitudinal member 10A is connected to vertebra VA by an attachment device 12A which may include a hook or a clamp and screw connector as are known in the art. Similarly, longitudinal member 10B is connected to vertebra VB by attachment device 12B in a manner known by those skilled in the art. One embodiment of a transverse connector 14 of the present invention is shown connected to and extending between longitudinal members 10A, 10B.

Transverse member 14 generally includes a first member 100 which connects to longitudinal member 10A, and a second member 200 which connects to longitudinal member 12B. First member 100 and second member 200 are connected to one another using a clamp 300. Transverse connector 14 extends along a longitudinal axis B which may be substantially perpendicular to longitudinal members 10A, 10B.

As best shown in FIGS. 2 through 5, first member 100 generally includes a body portion 110, an intermediate portion 130, a connector portion 150, and a clamp or set screw 180 which clamps longitudinal member 10A against connector portion 150. Body portion 110 includes an end wall 112, a pair of sidewalls 114, 116, a bottom wall 118, and a top wall 120. Top wall 120 includes a flat section 121 and a plurality of retaining surfaces 122. In one embodiment of the invention, retaining surfaces 122 include a plurality of parallel ridges, each having a triangular cross-section and extending perpendicularly between sidewalls 114, 116. As will be further explained below, the shape, number, and orientation of retaining surfaces 122 may be varied substantially from the embodiment shown. An opening 124 extends between top wall 120 and bottom wall 118 through retaining surfaces 122. In one embodiment of the invention, the opening is a bore which extends along an axis parallel to sidewalls 114, 116 and has a threaded inner surface 126.

Figure 3:
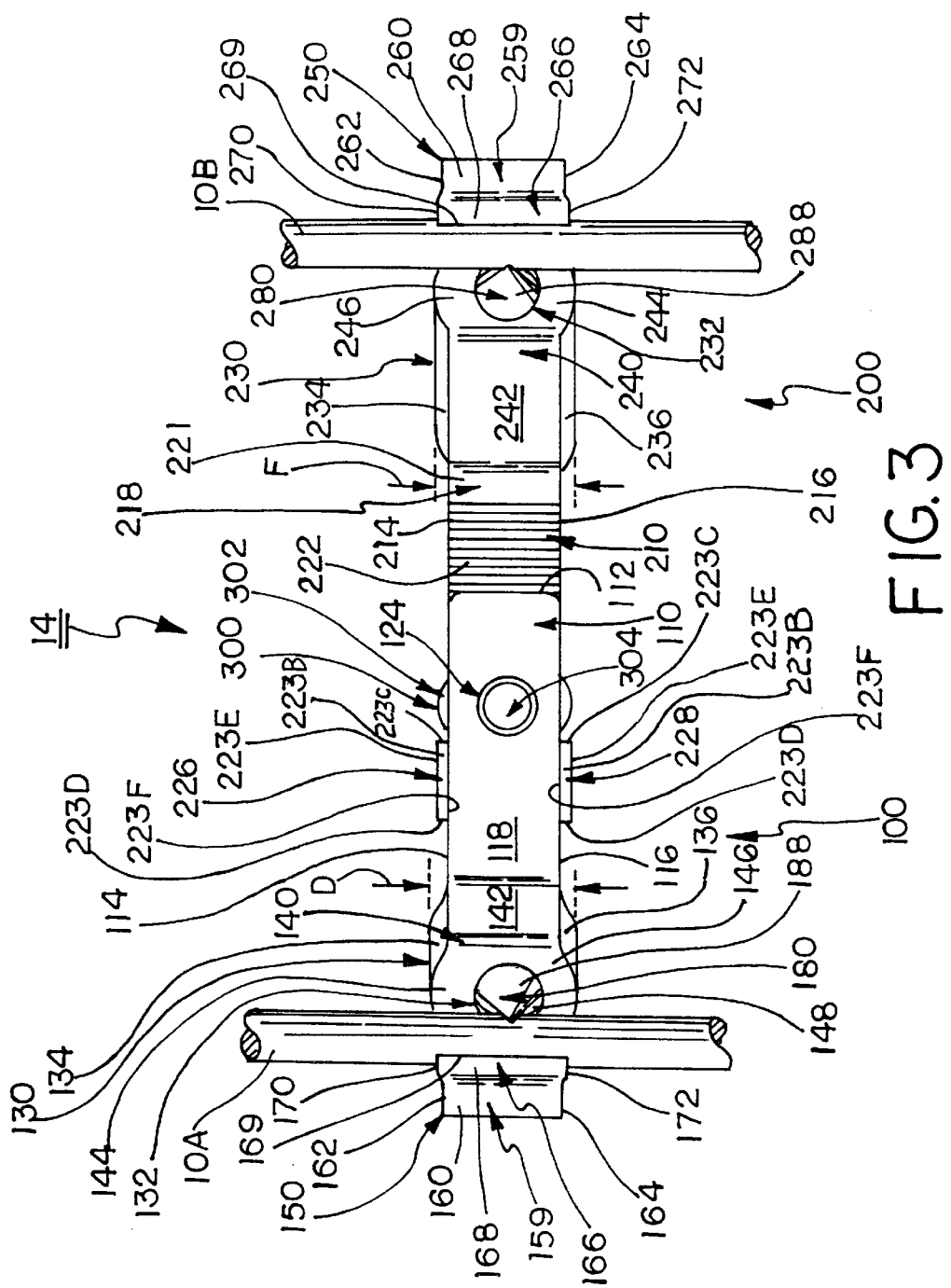
FIG. 3 is a bottom plan view of the transverse connector of FIG. 1.
Figure 4:
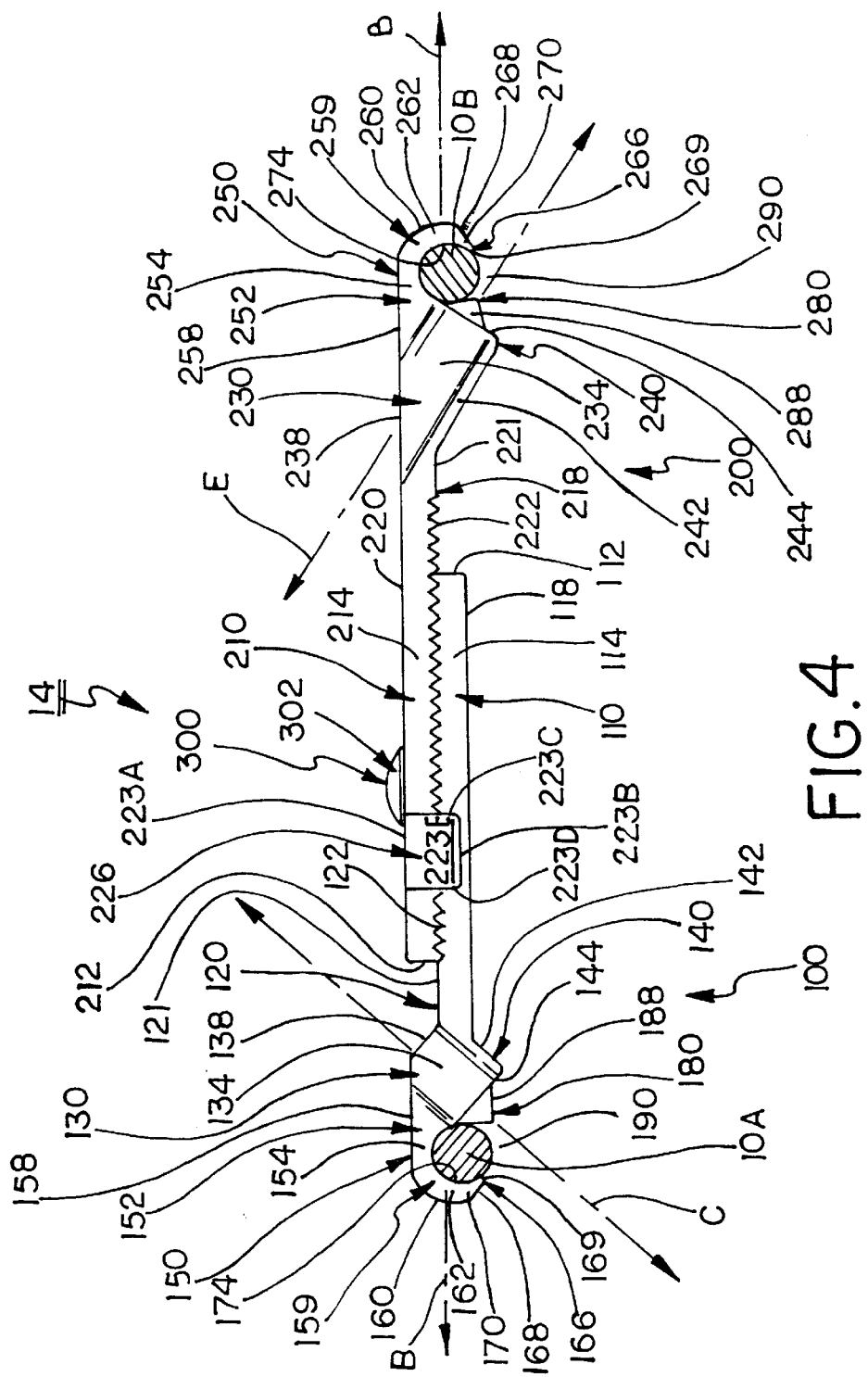
FIG. 4 is a side elevational view of the transverse connector of FIG. 1.

Intermediate portion 130 of first member 100 is integral with body portion 110 and extends therefrom to form a substantially cylindrical structure having an opening 132 therethrough. As best shown in FIG. 4, intermediate portion 130 and opening 132 are substantially centered on an axis C which is at an acute angle relative to longitudinal axis B. Intermediate portion 130 includes a curved sidewall 134 which extends from sidewall 114 of body portion 110, a curved sidewall 136 which extends from sidewall 116, and a top wall 138 which extends from flat section 121 of body portion 110. As best shown in FIG. 3, intermediate portion 130 also includes a bottom wall 140 which extends from bottom wall 118 of body portion 110 to form a flat 142 on the generally cylindrical shape of intermediate portion 130. Bottom wall 140 also includes a pair of curved segments 144, 146 which are substantially perpendicular to flat 142 and parallel to top wall 138 of intermediate portion 130. Opening 132 extends between top wall 138 and bottom wall 140 of intermediate portion 130 to form a bore with a threaded inner surface 148 (FIG. 5).

As best seen in FIG. 3, intermediate portion 130 includes a diameter D which is greater than the distance between sidewalls 114, 116 of body portion 110. This increased diameter permits use of a larger set screw 180 for connecting first member 100 to longitudinal member 10A, as described in greater detail below.

Referring again to FIGS. 2 through 5, first member 100 further includes a connector portion 150. In one embodiment of the invention, connector portion 150 extends from intermediate portion 130 to form a widened hook. Connector portion 150 includes a first segment 152 which lies in a plane substantially parallel to a plane extending through body portion 110 (as seen in FIGS. 4 and 5), a curved segment 159, and a tip segment 166. First segment 152 includes a pair of sidewalls 154, 156 which extend from curved sidewalls 134, 136 of intermediate portion 130, respectively, and a top wall 158 which extends from top wall 138 of intermediate portion 130 and lies in a plane substantially parallel to the plane of top wall 120 of body portion 110. As best seen in FIGS. 1 and 3, the distance between sidewalls 154, 156 of first segment 152 is less than diameter D of intermediate portion 130, and substantially the same as the distance between sidewalls 114, 116 of body portion 110.

Figure 5:
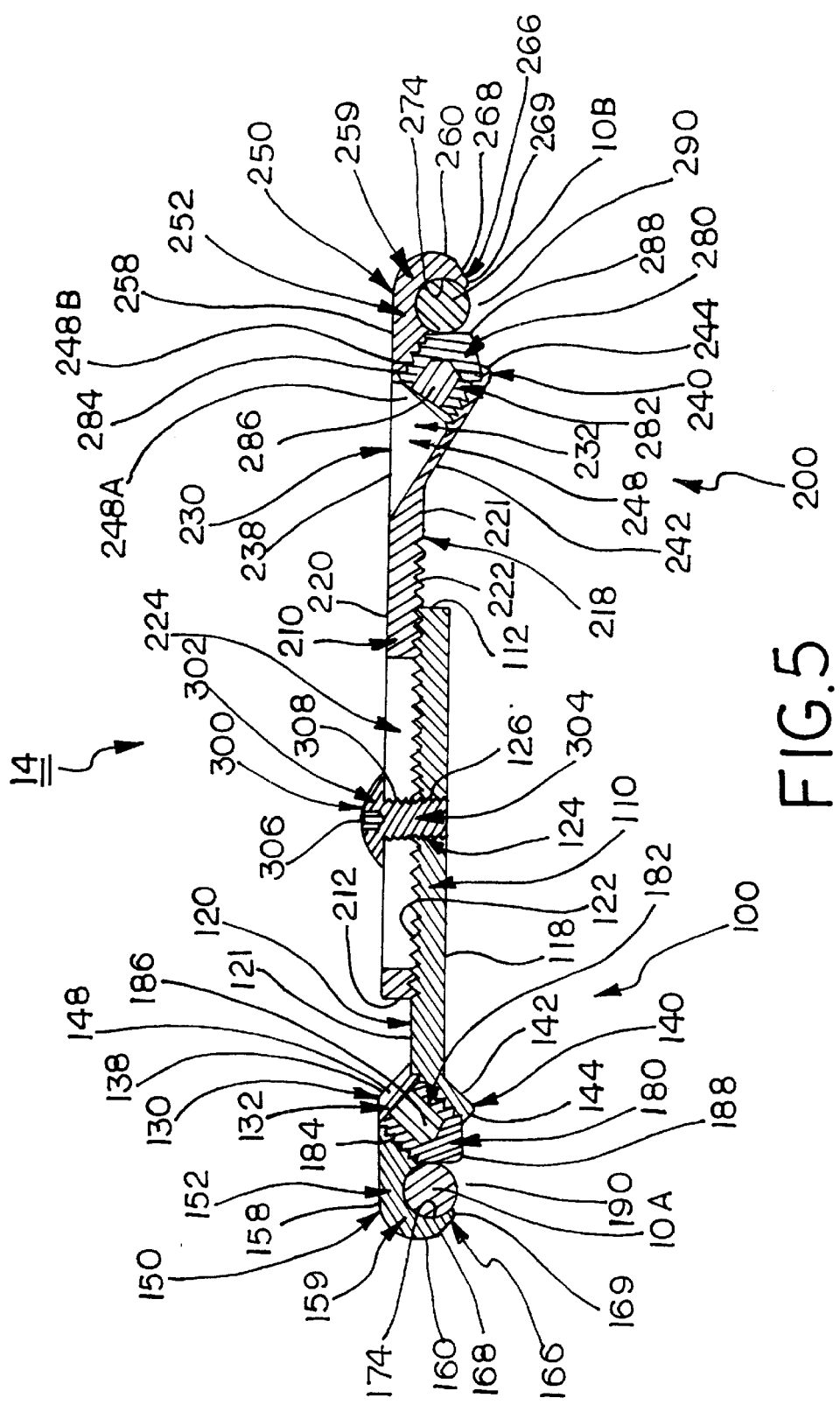
FIG. 5 is a cross-sectional view of the transverse connector of FIG. 1 taken substantially along line 5—5.

Referring now to FIGS. 4 and 5, curved segment 159 extends from first segment 152 in a curved manner downwardly adjacent a plane including bottom wall 118 of body portion 110. Curved segment 159 includes a curved outer wall 160 which extends from top wall 158 of first segment 152. Curved segment 159 also includes a pair of sidewalls 162, 164 which extend from sidewalls 154, 156 of first segment 152, respectively.

Tip segment 166 extends from curved segment 159 and includes a substantially flat bottom wall 168 which extends from curved outer wall 160 of curved segment 159, a curved end wall 169, and a pair of sidewalls 170, 172.

A curved engaging surface 174 is formed on the inside surface of first segment 152, curved segment 159, and tip segment 166 of connector portion 150. In one embodiment of the invention, engaging surface 174 has a constant radius which corresponds to the outer surface of longitudinal member 10A.

Set screw 180 includes a body 182 having threads 184, a drive recess 186, and a conical end surface 188. In the embodiment shown, threads 184 are formed to correspond to threaded inner surface 148 of opening 132. Additionally, drive recess 186 is shown as a hexagonal cavity for receiving an Allen wrench. Obviously, drive recesses 186 of various shapes, such as a slot, intersecting slots, or recesses of other shapes, may be incorporated into set screw 180 for turning the screw into and backing the screw out of opening 132 of intermediate portion 130.

Second member 200 generally includes a body portion 210, an intermediate portion 230, a connector portion 250, and a clamp or set screw 280 which clamps longitudinal member 10B against connector portion 250. Body portion 210 includes an end wall 212, a pair of sidewalls 214, 216, a bottom wall 218, and a top wall 220. The width of body portion 210 (as measured between sidewalls 214, 216) is substantially the same as the width of body portion 110 of first member 100. Body portion 210 further includes an adjustment opening 224 which extends between top wall 220 and bottom wall 218 and forms an elongated slot centered substantially on longitudinal axis B when first and second members are assembled.

Bottom wall 218 includes a flat portion 221 and plurality of retaining surfaces 222. In one embodiment of the invention, retaining surfaces 222 include a plurality of parallel ridges, each having a triangular cross-section and extending perpendicularly between sidewalls 214, 216. As best shown in FIG. 4, retaining surfaces 222 of bottom wall 218 engage retaining surfaces 122 of first member 110 when clamp 300 is used to attach first member 100 to second member 200. The engagement between the retaining surfaces prevents movement of the first member 100 and second member 200 relative to one another along the longitudinal axis B of the transverse connector 14. Rotational movement about clamp 300 is also prevented by retaining surfaces 122, 222. Obviously, matching retaining surfaces having a variety of cross-sectional shapes, for example, rectangular or curved, may readily be employed to prevent movement between first member 100 and second member 200. Additionally, retaining surfaces 122, 222 need not extend the entire widths of first member 100 and second member 200, respectively. As should be apparent from the foregoing, the number and spacing of retaining surfaces 122, 222 determines the number and spacing of selectable relative positions of first member 100 and second member 200 within the adjustment range provided by adjustment opening 224 of second member 200. Fewer retaining surfaces 122, 222 may be employed if fewer selectable positions are desired. Conversely, a larger number of more closely spaced retaining surfaces 122, 222 may be employed to provide a greater number of selectable positions within which transverse member 14 may be locked.

A pair of guides 226, 228 are attached to or integral with sidewalls 214, 216, respectively, of second member 200. Each guide 226, 228 is substantially rectangular and extends downwardly as viewed in FIG. 4 to overlap a respective sidewall 114, 116 of first member 100 when transverse connector 14 is assembled. Each guide 226, 228 includes an upper surface 223A which is planar with top wall 220, a lower surface 223B which is parallel to upper surface 223A, a pair of end surfaces 223C, 223D, an outer surface 223E, and an inner surface 223F. As shown in FIG. 3, the distance between inner surfaces 223F of guides 226, 228 is slightly greater than the distance between sidewalls 114, 116 of first body portion 100. As such, when clamp 300 is loosened and first member 100 is spaced apart from second member 200 such that retaining surfaces 122 do not engage retaining surfaces 222, the first and second members may be moved longitudinally relative to one another, yet remain in alignment on axis B because guides 226, 228 engage sidewalls 114, 116 of first member 100 to maintain such alignment. As will be further discussed below, the position of clamp 300 within adjustment opening 224 shifts as the first and second members are moved relative to one another.

Intermediate portion 230 of second member 200 is integral with body portion 210 and extends therefrom to form a substantially cylindrical structure having an opening 232 therethrough. Intermediate portion 230 and opening 232 are substantially centered on an axis E which is at an acute angle relative to longitudinal axis B. Intermediate portion 230 includes a first curved sidewall 234 which extends from sidewall 214 of body portion 210, a second curved sidewall 236 which extends from sidewall 216, a top wall 238 which is planar with and extends from top wall 220, and a bottom wall 240 which extends from flat portion 221 of bottom wall 218 to form a flat 242 on the generally cylindrical shape of intermediate portion 230 as best shown in FIG. 3. Bottom wall 240 of intermediate portion 230 also includes a pair of curved segments 244, 246 which are substantially perpendicular to flat 242 and lie in a plane perpendicular to axis E of intermediate portion 230.

Opening 232 extends between top wall 238 and bottom wall 240 of intermediate portion 230 to form a bore having an inner surface 248 (FIG. 5). Inner surface 248 includes a smooth portion 248A and a threaded portion 248B. As best seen in FIG. 3, intermediate portion 230 includes a diameter F which is greater than the distance between sidewalls 214, 216 of body portion 210. This increased diameter permits the use of a larger set screw 280 for connecting second member 200 to longitudinal member 10B, as described in greater detail below.

Referring again to FIGS. 2 through 5, second member 200 further includes a connector portion 250. In one embodiment of the invention, connector portion 250 extends from intermediate portion 230 to form a widened hook. Connector portion 250 includes a first segment 252 which is substantially planar with body portion 210 (as seen in FIGS. 4 and 5), a curved segment 259, and a tip segment 266. First segment 252 includes a pair of sidewalls 254, 256 which extend from sidewalls 234, 236 of intermediate portion 230, respectively, and a top wall 258 which extends from and is planar with top wall 238 of intermediate portion 230. As best seen in FIGS. 1 and 3, the distance between sidewalls 254, 256 of first segment 252 is less than the diameter of intermediate portion 230, and substantially the same as the distance between sidewalls 214, 216 of body portion 210.

Referring now to FIGS. 4 and 5, curved segment 259 extends from first segment 252 in a curved manner downwardly away from top wall 258. Curved segment 259 includes a curved outer wall 260 which extends from top wall 258. Curved segment 259 also includes a pair of sidewalls 262, 264 which extend from and lie in substantially the same plane as sidewalls 254, 256 of first segment 252.

Tip segment 266 extends from curved segment 259 and includes a substantially flat bottom wall 268 which extends from curved outer wall 260 of curved segment 259, a curved end wall 269, and a pair of sidewalls 270, 272.

A curved engaging surface 274 is formed on the inside surface of first segment 252, curved segment 259, and tip segment 266 of connector portion 250. In one embodiment of the invention, engaging surface 274 has a constant radius which corresponds to the outer surface of longitudinal member 10B.

Set screw 280 includes a body 282 having threads 284, a drive recess 286, and a conical end surface 288. In the embodiment shown, threads 284 are formed to correspond to threaded inner surface 248B of opening 232. Additionally, drive recess 286 is shown as a hexagonal cavity for receiving an Allen wrench. Obviously, drive recesses 286 of various shapes, such as a slot, intersecting slots, or recesses of other shapes, may be incorporated into set screw 280 for turning the screw into and backing the screw out of opening 232 of intermediate portion 230.

Transverse connector 14 also includes a clamp 300 which, in one embodiment of the invention, is a screw including a head 302 and a body 304. Head 302 includes a drive recess 306 which is shown as a hexagonal opening for receiving an Allen wrench. Of course, various other drive recess configurations may be employed. Body 304 includes threads 308 sized to mate with threads 126 of opening 124 formed in first member 100. The outer diameter of threads 308 is slightly less than the inner diameter of adjustment opening 224 formed in second member 200. Accordingly, clamp 300 may be inserted through adjustment opening 224 and turned into opening 124 of first member 100. When clamp 300 is tightened into opening 124, head 302 engages top wall 220 of body portion 210 to urge retaining surfaces 222 into engagement with retaining surfaces 122 of body portion 110. As such, when clamp 300 is in a tightened position, first member 100 and second member 200 are locked into position relative to one another as explained above.

In operation, traverse member 14 is connected to longitudinal members 10A, 10B by backing set screws 180, 280 out of openings 132, 232 such that conical end surfaces 188, 288 are sufficiently spaced from engaging surfaces 174, 274 to form gaps 190, 290 large enough to receive longitudinal members 10A, 10B. Connector portions 150, 250 are placed onto longitudinal members 10A, 10B such that longitudinal members 10A, 10B are situated within and contacting engaging surfaces 174, 274. Set screws 180, 280 are then turned into openings 132, 232 until conical end surfaces 188, 288 engage longitudinal members 10A, 10B, thereby clamping the longitudinal members within connector portions 150, 250 of first member 100 and second member 200, respectively.

The distance between longitudinal members 10A, 10B may be adjusted or set by loosening clamp 300 sufficiently to provide clearance between retaining surfaces 122 of body portion 110 and retaining surfaces 222 of body portion 210. When clamp 300 is in a loosened position, longitudinal members 10A, 10B may be urged away from one another or pulled toward one another into a desired orientation. During this adjustment, guides 226, 228 of second member 200 slide along sidewalls 214, 216 of first member 100 to maintain alignment between first member 100 and second member 200 as described above. Additionally, clamp body 304 shifts within adjustment opening 244. The range of adjustment is limited by the length of adjustment opening 224. Body portion 210 overlaps body portion 110 throughout the entire range of adjustment. After the desired orientation is reached, clamp 300 is tightened into opening 124 of body portion 110 until retaining surfaces 122 engage retaining surfaces 222 and the first and second members are locked into position relative to one another.

Figure 6:
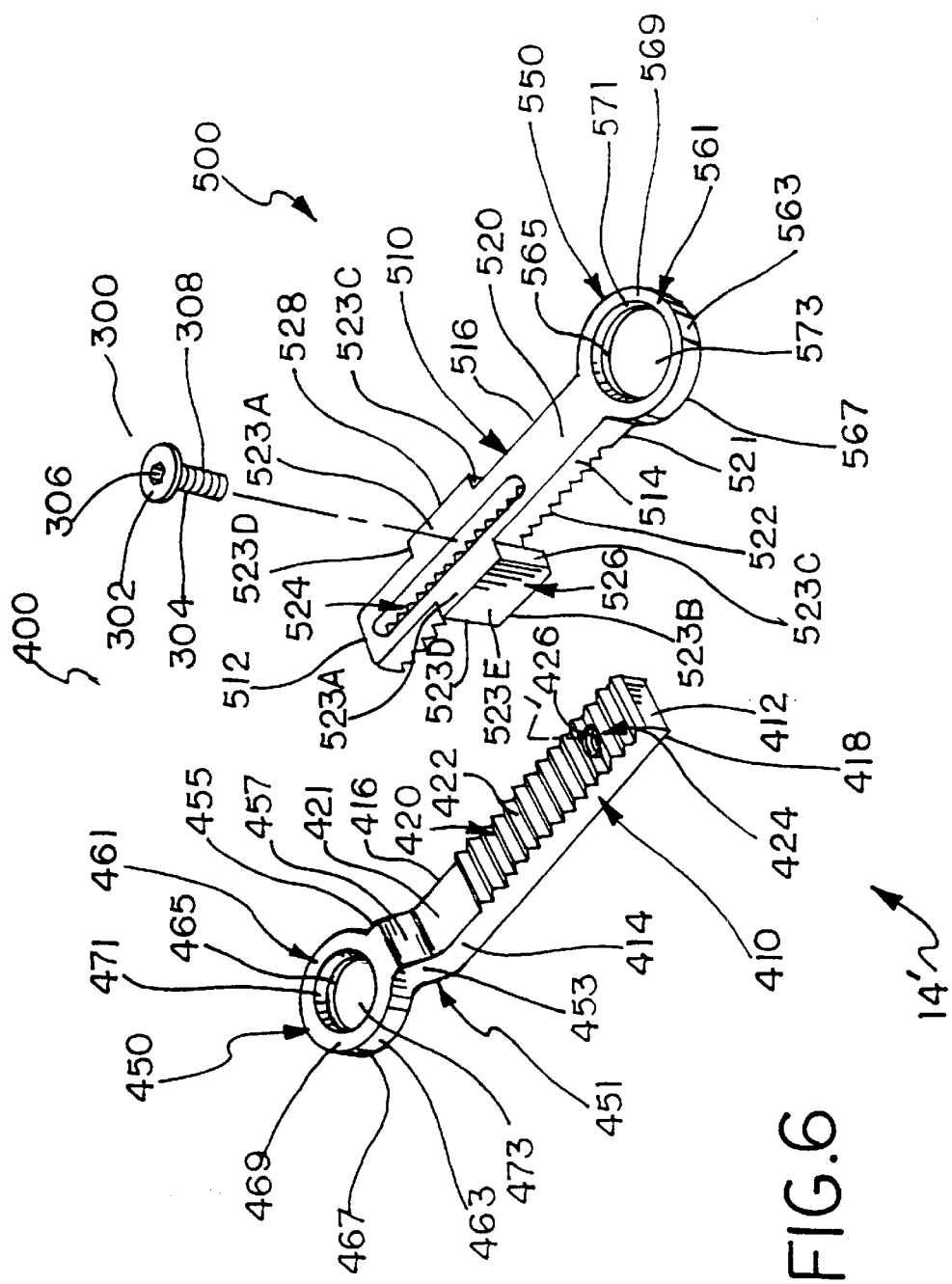
FIG. 6 is an exploded perspective view of another embodiment of the transverse connector of the present invention.
Figure 7:
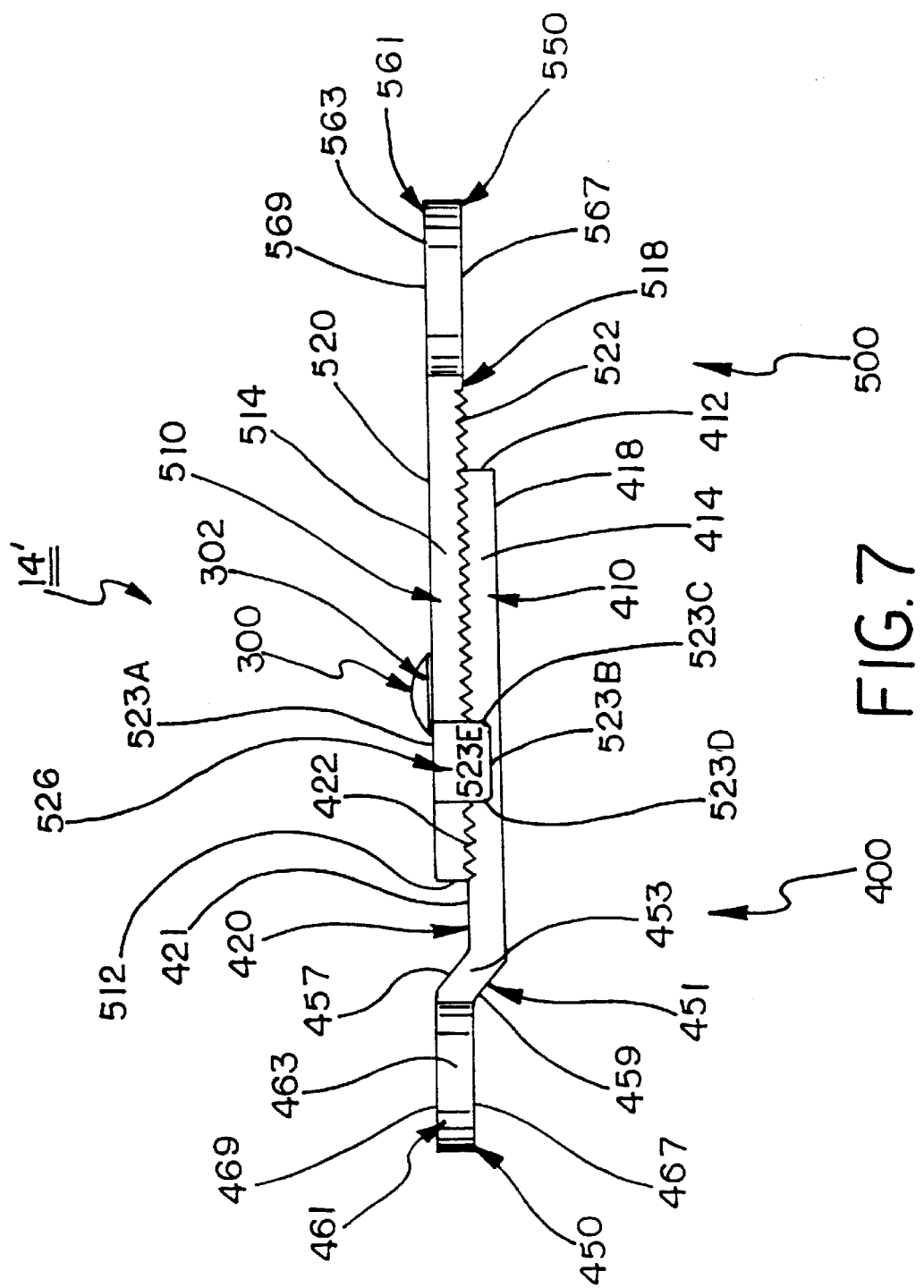
FIG. 7 is a side elevational view of the transverse connector of FIG. 6.

FIGS. 6 and 7 illustrate another embodiment of the transverse connector according to the present invention. Transverse connector 14ℓ generally includes a first member 400, a second member 500, and a clamp 300 for connecting the first and second members together. First member 400 is similar to first member 100. Likewise, second member 500 is similar to second member 200, discussed above. To simplify this description, the reference designations of features of first member 100 which are similar to features of first member 400 have been retained, except that the first digit of the reference designation has been changed from a 1 to a 4. Similarly, the first digit of like components and features of second member 200 and second member 500 has been changed from a 2 to a 5. Only the differences between transverse connector 14 and transverse connector 14ℓ will be described in detail below.

First member 400 includes a connector portion 450 instead of the hook and screw configuration of first member 100. Connector portion 450 includes an angled segment 451 extending from body portion 410 which includes sidewalls for 453, 455 which extend from sidewalls 414, 416, respectively. Angled segment 451 also includes an upper surface 457 and lower surface 458 which extend from flat section 421 and bottom wall 418, respectively. As best shown in FIG. 7, angled segment 451 extends upwardly away from bottom wall 418.

Connector portion 450 also includes a connector ring 461 which extends from angled segment 451 and lies in a plane substantially parallel to a plane including bottom wall 418, as best shown in FIG. 7. Connector ring 461 includes a substantially circular outer side surface 463, a circular inner side surface 465, a bottom surface 467, a top surface 469, and a circular chamfered surface 471 extending between circular inner surface 465 and top surface 469. Connector ring 461 of connector portion 450 defines a central opening 473 for receiving a pedicle screw and clamp in a manner commonly known in the art.

Connector portion 550 of second member 500 similarly includes a connector ring 561. Connector ring 561 includes a substantially circular outer side surface 563 which extends between sidewalls 514, 516 of second member body portion 510. Connector ring 561 also includes a circular inner side surface 565, a bottom surface 567 extending from flat section 521, a top surface 569 extending from top wall 520, and circular chamfered surface 571 extending between inner side surface 565 and top surface 569. Connector ring 561 defines a circular opening 573 for receiving a pedicle screw clamped in a manner commonly known in the art.

As best seen in FIG. 7, connector ring 561 is substantially planar with body portion 510 of second member 500. When transverse connector 14ℓ is assembled in the manner described above, connector ring 461 of first member 400 is substantially planar with connector ring 561 of second member 500. First member 400 and second member 500 may be adjusted relative to one another along axis B by loosening claim 300 in the manner described above.

As should be apparent to one of ordinary skill in the art, first member 100 of transverse connector 14 may be substituted for first member 400 of transverse member 14'. Similarly, second member 200 of transverse connector 14 may be substituted second member 500 of transverse connector 14ℓ. As such, a transverse connector according to the present invention may extend between longitudinal members, spinal hooks, and/or pedicle screw and clamp assemblies, or any combination thereof.

While this application has been described as having exemplary embodiments, this application is intended to cover any variations, uses, or adaptations using its general principles. Further, this application is intended to cover such departures from the present disclosure as come within the known or customary practice within the art to which it pertains. The spirit and scope of the invention are to be limited only by the terms of the appended claims.

Figure 8:
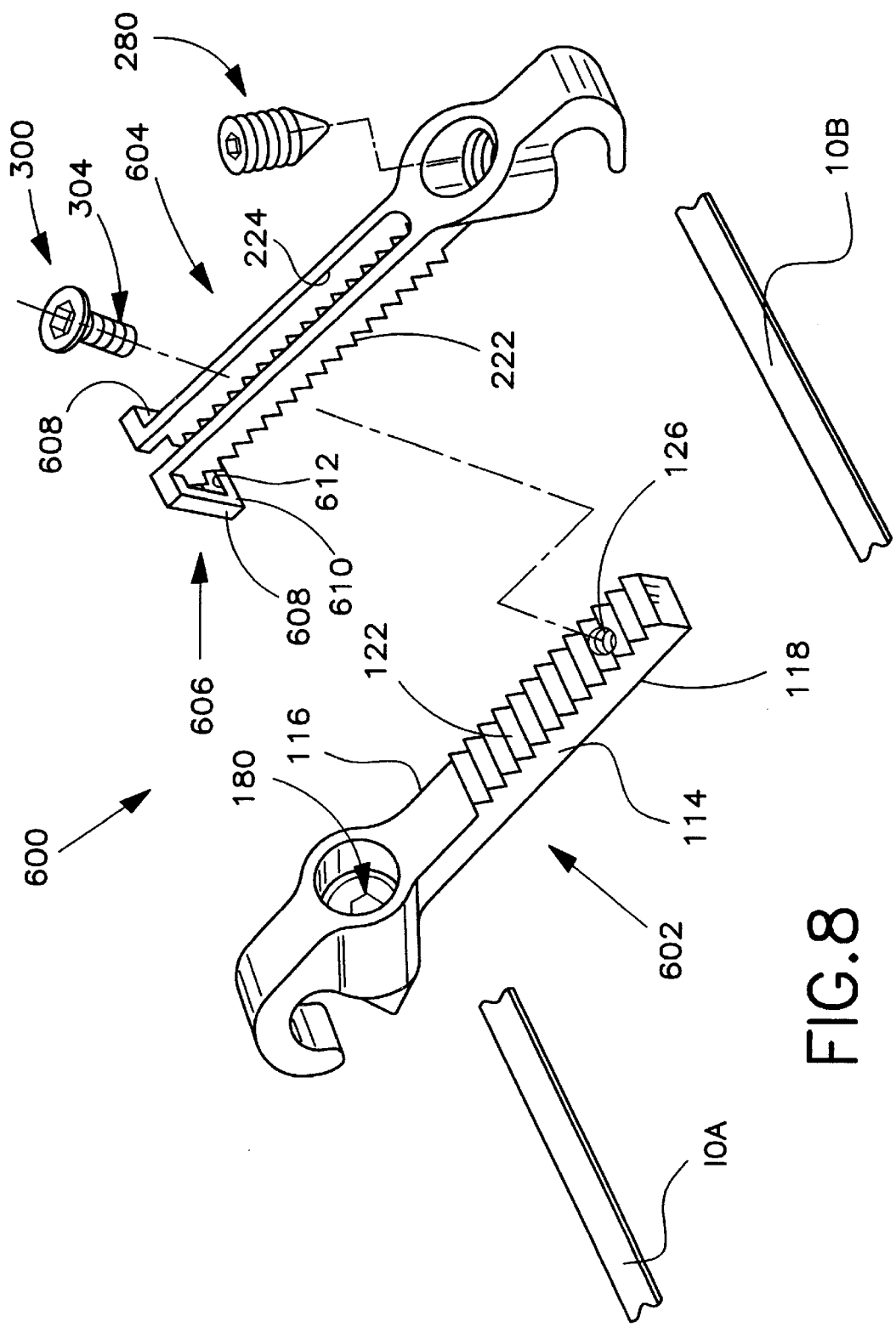
FIG. 8 is an exploded perspective view of yet another embodiment of the transverse connector of the present invention.
Figure 9:
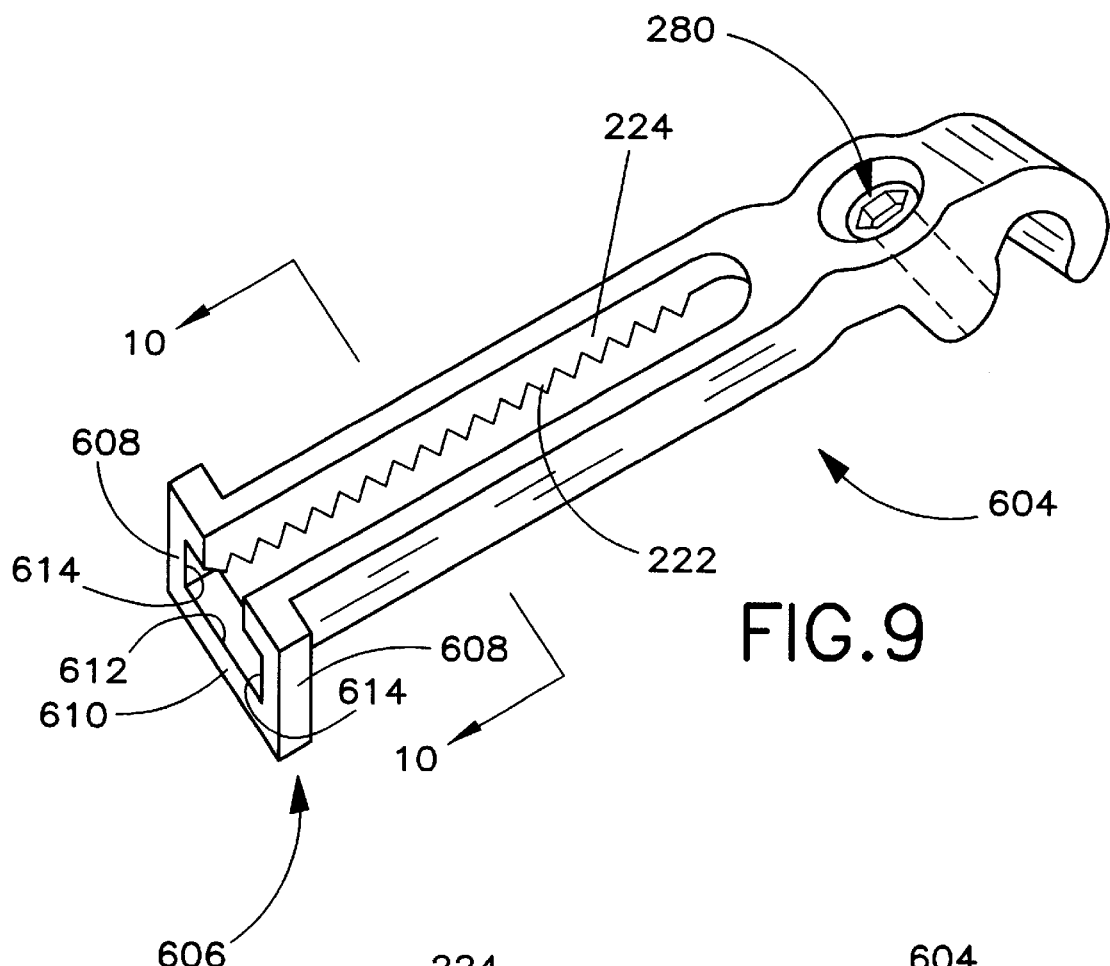
FIG. 9 is another perspective view of the second member of the transverse connector of FIG. 8.
Figure 10:
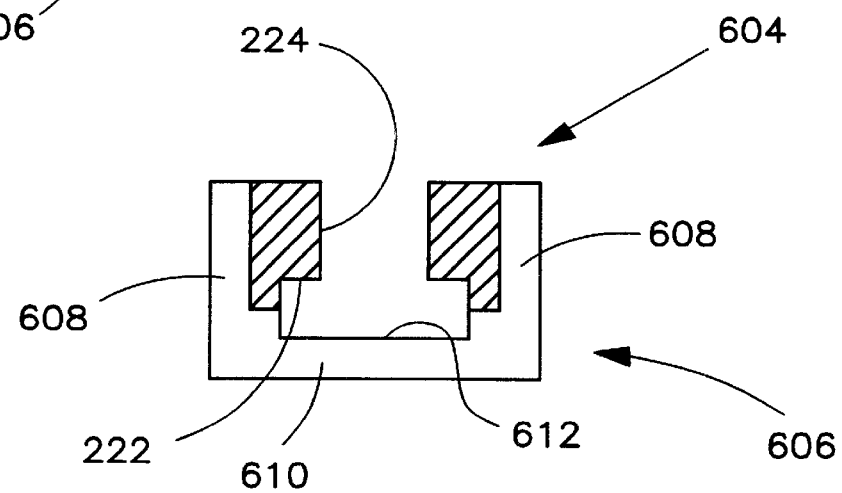
FIG. 10 is a cross-sectional view of the second member taken along the lines 10—10 of FIG. 9 as viewed in the direction of the arrows.

For example, FIGS. 8–10 show yet another alternative embodiment which incorporates the features of the present invention therein. In particular, a transverse member 600 includes a first member 602 which connects to longitudinal member 10A, and a second member 604 which connects to longitudinal member 10B in a manner similar to that hereinbefore described with respect to the connection of the first member 100 and the second member 200, respectively, to longitudinal members 10A, 10B of FIGS. 1–5. In fact, the first member 602 is substantially identical to the first member 100 of FIGS. 1–5. As a result, the reference numerals used to identify components of the first member 100 are also relevant to identify components of the first member 602. However, since such components have been described hereinabove with respect to FIGS. 1–5, the first member 602 will not be further described in detail. Moreover, the second member 604 is somewhat similar to the second member 200 of FIGS. 1–5. As a result, some of the reference numerals used to identify components of the second member 200 are also relevant to identify components of the second member 604. Since such components have been described hereinabove with respect to FIGS. 1–5, only the new features and components of the second member 604 will be further described in detail.

The new features of the second member 604 in comparison to the second member 200 (see FIGS. 1–5) are shown in FIGS. 8–10. In particular, the second member 604 includes a stabilizer assembly 606 which is located at an end of the second member 604 as shown in FIGS. 8 and 9. The stabilizer assembly 606 includes two downwardly extending members 608 and a transverse member 610 which are all connected to each other in a continuous and integral fashion as shown in FIGS. 8 and 9. The two downwardly extending members 608 and the transverse member 610 collectively form a passage 612 through which the first member 602 may be advanced.

During use, the first member 602 is advanced a distance through passage 612 so that a portion of the retaining surfaces 122 of the first member 602 axially align with a portion of the retaining surfaces 222 of the second member 604. Thereafter, the body 304 of the screw of the clamp 300 is advanced through adjustment opening 224 and into meshing engagement with the threads 126 of the first member 602 so as to secure the first member 602 to the second member 604. It should be noted that while the first member 602 is secured to the second member 604 in this manner, the transverse member 610 of the stabilizer assembly 606 contacts the bottom wall 118 of the first member 602 so as to prevent the first member 602 from wobbling or otherwise moving relative to the second member 604 when force is applied to the transverse member 600.

Also, in order to further prevent the first member 602 from wobbling or otherwise moving relative to the second member 604 when force is applied to the transverse member 600, it is possible to provide a groove (not shown) in each of the sidewalls 114, 116 of the first member 602, and a cooperating tongue or flange (not shown) on an interior side 614 of each of the downwardly extending members of the stabilizer assembly 606 of the second member 604. As a result, when the first member 602 is advanced a distance through passage 612, the tongues of the second member would be respectively positioned within the grooves of the first member 602.

FIGS. 11 and 12 illustrate still another embodiment of the transverse connector according to the present invention. Transverse connector 700 is substantially identical to transverse connector 14, and therefore only the differences between transverse connector 700 and transverse connector 14 will be discussed in detail below.

Transverse connector 700 includes a connector portion 702 having an engaging surface 704. Engaging surface 704 includes an arcuate wall segment 710 and substantially flat wall segments 706 and 708. Arcuate wall segment 710 is integral with each wall segment 706 and 708 such that arcuate wall segment 710 is interposed between wall segments 706 and 708. It should be appreciated that arcuate wall segment 710 and wall segments 706 and 708 collectively define engaging surface 704. It should further be appreciated that arcuate wall segment 710, wall segment 706, and wall segment 708 are spatially orientated relative to one another such that engaging surface 704 defines a substantially V-shaped cross section with arcuate wall segment 710 being located at the apex 712 of the V.

Engaging surface 704 is utilized in a similar manner as described above for curved engaging surface 174. In particular, a longitudinal member 714 is biased toward engaging surface 704 in the direction indicated by arrow 716 with a set screw (not shown) such that longitudinal member 714 is placed in contact with wall segments 706 and 708. However, it should be understood that having engaging surface 704 constructed such that engaging surface 704 defines a substantially V-shaped cross section is an important aspect of the present invention. Specifically, the V-shaped configuration defined by engaging surface 704 allows longitudinal members having relatively large or small diameters to be accepted and securely held within connector portion 702. As shown in FIGS. 11 and 12, respectively, longitudinal member 714 has a diameter $D_1$ and longitudinal member 716 has a diameter $D_2$ which is greater than diameter $D_1$. However, even though longitudinal members 714 and 716 have different diameters (i.e. $D_2>D_1$) the V-shaped configuration defined by engaging surface 704 allows both longitudinal members to be accepted and securely held within connector portion 702 when biased in the direction indicated by arrows 716 by the set screw. Note that it is preferred that arcuate wall segment 710 always has a radius that is smaller than the smallest diameter longitudinal member so as to ensure that the longitudinal member is securely held within connector portion 702 when biased in the direction indicated by arrows 716 by the set screw. Based upon the above discussion it should be appreciated that engaging surface 704 allows transverse connector 700 to be easily and conveniently utilized with any one of a plurality of transverse members having different sized diameters.

What is claimed is:

1. A transverse connector, comprising:
a first member including a first elongated body portion and a first connector portion, said first elongated body portion having (i) a first lateral side surface, (ii) a second lateral side surface, and (iii) a lower contact surface;
a second member including a second elongated body portion and a second connector portion, said second elongated body portion having an upper contact surface; and
a clamp which is movable into (i) a tightened position in which said lower contact surface is forced in contact with said upper contact surface thereby locking the first member in relation to said second member, and (ii) a loosened position which permits said lower contact surface to be spaced apart from said upper contact surface whereby said first member may be adjusted relative to said second member,
wherein said first member further includes (i) a first lateral guide which is integral with said first lateral sidewall of said first elongated body, and (ii) a second lateral guide which is integral with said second lateral sidewall of said first elongated body, and
wherein each of said first lateral guide and said second lateral guide extends vertically below said lower contact surface so as to define a guide space therebetween, and
wherein said second elongated body portion is positioned in said guide space when said clamp is in said tightened position.

2. The transverse connector of claim 1, wherein:
said first elongated body has a first end attached to said first connector portion and a second end defining an end surface, and
each of said first lateral guide and said second lateral guide are spaced apart inwardly from said end surface.

3. The transverse connector of claim 1, wherein:
said second elongated body portion further has a bottom surface,
said first lateral guide has a first lower guide surface and said second lateral guide has a second lower guide surface, and
said bottom surface is positioned vertically below both said first lower guide surface and said second lower guide surface when said clamp is in said tightened position.

4. The transverse connector of claim 3, wherein:
said first lateral guide further has a first upper guide surface, said second lateral guide further has a second upper guide surface, said first lower guide surface is parallel to said first upper guide surface, and said second lower guide surface is parallel to said second upper guide surface.

5. The transverse connector of claim 1, wherein:

said lower contact surface of said first elongated body portion includes a rail segment defining a plurality of parallel rails, and said rail segment extends between said first lateral guide and said second lateral guide.

6. The transverse connector of claim 1, wherein:

said first lateral guide has a first lateral outer surface, said second lateral guide has a second lateral outer surface, and each of said first lateral outer surface and said second lateral outer surface possesses a substantially rectangular shape.

7. The transverse connector of claim 1, comprising:

said first lateral guide further has a first upper guide surface, said second lateral guide further has a second upper guide surface, said first elongated body portion further has a top surface, and said first upper guide surface, said second upper guide surface, and said top surface are coplanar in relation to each other.

8. The transverse connector of claim 1, wherein:

said first elongated body portion has an adjustment slot defined therein which is configured to receive said clamp, and said adjustment slot is interposed between said first lateral guide and said second lateral guide.

9. The transverse connector of claim 1, wherein:

said clamp is a threaded fastener, and said second elongated body portion has a threaded opening defined therein which is configured to receive said threaded fastener.

10. A transverse connector, comprising:

a first member including a first elongated body portion and a first connector portion, said first elongated body portion having a lower contact surface;

a second member including a second elongated body portion and a second connector portion, said second elongated body portion having an upper contact surface; and a clamp which is movable into (i) a tightened position in which said lower contact surface is forced in contact with said upper contact surface, and (ii) a loosened position which permits said lower contact surface to be spaced apart from said upper contact surface, wherein said first member further includes a first lateral guide and a second lateral guide each being attached to said first elongated body, and wherein each of said first lateral guide and said second lateral guide extends vertically below said lower contact surface so as to define a guide space therebetween, and wherein said second elongated body portion is positioned in said guide space when said clamp is in said tightened position.

11. The transverse connector of claim 10, wherein:

said first elongated body has a first end attached to said first connector portion and a second end defining an end surface, and each of said first lateral guide and said second lateral guide are spaced apart inwardly from said end surface.

12. The transverse connector of claim 10, wherein:

said second elongated body portion further has a bottom surface, said first lateral guide has a first lower guide surface and said second lateral guide has a second lower guide surface, and said bottom surface is positioned vertically below both said first lower guide surface and said second lower guide surface when said clamp is in said tightened position.

13. The transverse connector of claim 12, wherein:

said first lateral guide further has a first upper guide surface, said second lateral guide further has a second upper guide surface, said first lower guide surface is parallel to said first upper guide surface, and said second lower guide surface is parallel to said second upper guide surface.

14. The transverse connector of claim 10, wherein:

said lower contact surface of said first elongated body portion includes a rail segment defining a plurality of parallel rails, and said rail segment extends between said first lateral guide and said second lateral guide.

15. The transverse connector of claim 10, wherein:

said first lateral guide has a first lateral outer surface, said second lateral guide has a second lateral outer surface, and each of said first lateral outer surface and said second lateral outer surface possesses a substantially rectangular shape.

16. The transverse connector of claim 10, comprising:

said first lateral guide further has a first upper guide surface, said second lateral guide further has a second upper guide surface, said first elongated body portion further has a top surface, and said first upper guide surface, said second upper guide surface, and said top surface are coplanar in relation to each other.

17. The transverse connector of claim 10, wherein:

said first elongated body portion has an adjustment slot defined therein which is configured to receive said clamp, and said adjustment slot is interposed between said first lateral guide and said second lateral guide.

18. The transverse connector of claim 10, wherein:

said clamp is a threaded fastener, and said second elongated body portion has a threaded opening defined therein which is configured to receive said threaded fastener.

* * * * *